(12) United States Patent
Ren et al.

(10) Patent No.: US 11,566,048 B2
(45) Date of Patent: Jan. 31, 2023

(54) PEPTIDE THAT REGULATES FAT METABOLISM AND METHOD FOR REGULATING FAT METABOLISM

(71) Applicant: SHENZHEN INSTITUTES OF ADVANCED TECHNOLOGY, Shenzhen (CN)

(72) Inventors: Peigen Ren, Shenzhen (CN); Jian Zhang, Shenzhen (CN); Bin Teng, Shenzhen (CN); Jian Li, Shenzhen (CN); Zhenyu Yao, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 0 days.

(21) Appl. No.: 17/359,370

(22) Filed: Jun. 25, 2021

(65) Prior Publication Data

US 2021/0395307 A1 Dec. 23, 2021

Related U.S. Application Data

(63) Continuation of application No. 16/572,584, filed on Sep. 16, 2019, now Pat. No. 11,098,083, which is a continuation of application No. PCT/CN2017/076886, filed on Mar. 16, 2017.

(51) Int. Cl.
*C07K 7/08* (2006.01)
*A61K 38/00* (2006.01)
*A61P 1/16* (2006.01)
*A61P 3/00* (2006.01)
*A61P 3/04* (2006.01)
*A61P 3/06* (2006.01)
*A61P 3/10* (2006.01)

(52) U.S. Cl.
CPC ............... *C07K 7/08* (2013.01); *A61K 38/00* (2013.01)

(58) Field of Classification Search
CPC ............ C07K 7/08; A61K 38/00; A61P 1/16; A61P 3/00; A61P 3/04; A61P 3/06; A61P 3/10
See application file for complete search history.

(56) References Cited

U.S. PATENT DOCUMENTS

| 7,666,424 B2* | 2/2010 | Cheung ............... A61K 47/6865 424/178.1 |
| 8,883,739 B2* | 11/2014 | Karsenty ................. A61P 15/16 514/21.3 |
| 8,969,289 B2* | 3/2015 | Gosselin ................... A61P 3/06 530/300 |
| 9,228,010 B2* | 1/2016 | Li ............................ A61P 11/00 |
| 2011/0117658 A1 | 5/2011 | Yang et al. |

FOREIGN PATENT DOCUMENTS

| CN | 2010503681 A | 2/2010 |
| CN | 103554249 A | 2/2014 |
| JP | 1992225162 A | 8/1992 |
| JP | 2017039652 A | 2/2017 |
| WO | WO2016081728 A1 | 5/2016 |

OTHER PUBLICATIONS

Machine English translation of CN 103554249, pp. 1-15. (Year: 2014).*
High-performance liquid chromatography-mass spectrometry of an osteocalcin derivative : J. Chromatogr.A,1999, vol. 846,pp. 49-57.
Sandwich immunoassay specific for the N-terminal sequence of osteocalcin: J. Immunol. Methods,1995,vol. 184, pp. 231-240.
Osteocalcin and insulin secretion: Kijo no Kami, iyo Kawachi, Tomoyo Takeuchi, Hirota Hirata, 2015,vol. 145, pp. 201-2015.
Japanese Decision to Grant a Patent,Japanese Application No. 2019550656, dated Feb. 8, 2022 (6 pages).
Korean Notice of Final Rejection, Korean Application No. 10-2019-7029172, dated Mar. 24, 2022 (13 pages).

* cited by examiner

*Primary Examiner* — Julie Ha

(57) ABSTRACT

A peptide for regulating fat metabolism is described. The peptide is selected from the group consisting of: YLGASVPSPDPLEP (SEQ ID NO: 1); YLNNGLGAPA-PYPDPLEP (SEQ ID NO: 4); PDPLEP (SEQ ID NO: 14); and PSPDPLEP (SEQ ID NO: 16).

1 Claim, 11 Drawing Sheets

Specification includes a Sequence Listing.

PEPTIDE THAT REGULATES FAT METABOLISM AND METHOD FOR REGULATING FAT METABOLISM

CROSS REFERENCE TO RELATED APPLICATIONS

This is a divisional application of U.S. patent application Ser. No. 16/572,584 filed on Sep. 16, 2019, which is a continuation-application of PCT Application No. PCT/CN2017/076886, filed on Mar. 16, 2017.

STATEMENT REGARDING SEQUENCE LISTING

The Sequence Listing associated with this application is part of the application and is provided in text in the form of an ASCII text file in lieu of a paper copy, and is hereby incorporated by reference into the specification. The name of the text file containing the Sequence listing is PeptideSequenceListing. The size of the text file is 4 kilobytes, was created on Sep. 8, 2021, and is being electronically submitted via EFS-Web.

TECHNICAL FIELD

The present disclosure relates to the field of biomedicine, and in particular to a peptide for regulating fat metabolism.

BACKGROUND

Obesity is a major and growing health problem worldwide. Obesity is also a risk factor for the development of many common diseases such as atherosclerosis, hypertension, type 2 diabetes, dyslipidemia, coronary heart disease, osteoarthritis and various malignancies. It also causes more serious problems by reducing exercise capacity and quality of life. Occurrence of the obesity and the diseases caused by the obesity are growing in all developed countries.

Fatty liver refers to a lesion caused by excessive accumulation of fat in hepatocytes. There are many causes of the fatty liver, such as alcoholism, unreasonable diet, and sedentariness. It witnesses increasing incidence in China and constitutes a threat to people's health.

However, the current drugs and methods for treating the obesity and the diseases caused by the obesity, including nonalcoholic fatty liver (NAFLD), have certain deficiencies, so it needs to develop medicines and methods with better efficacy and lower side effects for the treatment of the obesity and the NAFLD.

Osteocalcin (OCN) is a vitamin K-dependent calcium-binding protein and a non-collagen acidic glycoprotein synthesized and secreted by osteoblasts, the vitamin K-dependent glutamate residue in its molecule is an important functional group for the OCN to bind with $Ca^{2+}$.

SUMMARY OF THE DISCLOSURE

In order to provide a more effective treatment for the obesity-induced NAFLD and other obesity-induced diseases, the present disclosure may provide a peptide for regulating fat metabolism, wherein the peptide is a variant of a SEQ ID NO: 2 having an amino acid sequence of YLYQWLGAPVPYPDPLEP, the variant comprises peptides selected from the group consisting of: (a) a first amino acid sequence consisting of the SEQ ID NO: 2, no more than 5 amino acids inserted to a C-terminal of the SEQ ID NO: 2, and no more than 5 amino acids inserted to a N-terminal of the SEQ ID NO: 2; (b) a second amino acid sequence consisting of a modified SEQ ID NO: 2, no more than 5 amino acid sequence inserted to a C-terminal of the modified SEQ ID NO: 2, and no more than 5 amino acid sequence inserted to a N-terminal of the modified SEQ ID NO: 2, wherein the modified SEQ ID NO: 2 is obtained by: deleting the Y (Tyr) at a position 3 of the SEQ ID NO: 2 or substituting the position 3 of the SEQ ID NO: 2 to be Asn or Asp; deleting the Q (Gln) at a position 4 of the SEQ ID NO: 2 or substituting the position 4 of the SEQ ID NO: 2 to be Asn, His, Pro, or Ser; deleting the W (Trp) at a position 5 of the SEQ ID NO: 2 or substituting the position 5 of the SEQ ID NO: 2 to be Gly; deleting the L (Leu) at a position 6 of the SEQ ID NO: 2; substituting the P (Pro) at a position 9 of the SEQ ID NO: 2 to be Ser; substituting the V (Val) at a position 10 of the SEQ ID NO: 2 to be Ala; substituting the Y (Tyr) at a position 12 of the SEQ ID NO: 2 to be Ser; substituting the P (Pro) at a position 15 of the SEQ ID NO: 2 to be Thr; and a total number of positions being substituted and deleted in the second amino acid sequence defined in (b) is less than 4; and (c) a third amino acid sequence consisting of at least 6 contiguous amino acids of the SEQ ID NO: 2 or the modified SEQ ID NO: 2.

for 6 weeks on a level of alanine aminotransferases (ALT) in blood of the DIO-NAFLD mice fed with HFD, comparing with that in the mice of the HFD control group, wherein each group includes six mice (according to statistical analysis, *: $P<0.05$ and **: $P<0.01$, compared with the HFD control group).

Figure 4A:
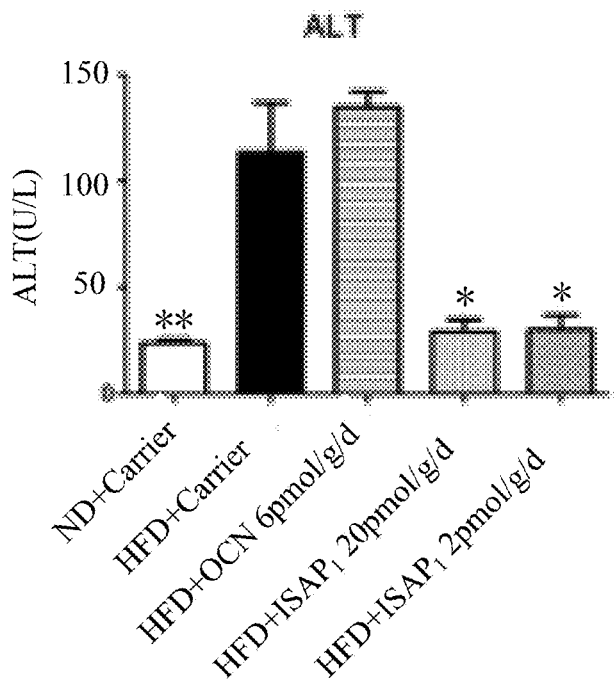
FIG. 4A shows an effect of daily i.p. injection of various concentrations of SEQ ID NO.17 and OCN (mouse OCN)
Figure 4B:
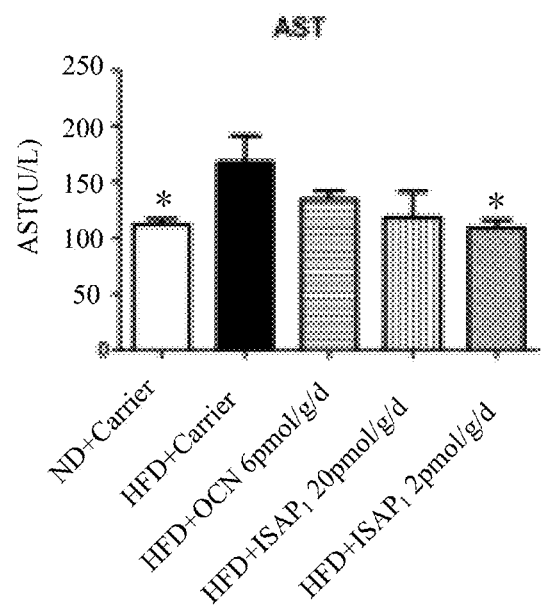

FIG. 4B shows an effect of daily i.p. injection of various concentrations of SEQ ID NO.17 and OCN (mouse OCN) for 6 weeks on a level of alkaline phosphatases (ALP) in blood of the DIO-NAFLD mice fed with HFD, comparing with that in the mice of the HFD control group, wherein each group includes six mice (according to statistical analysis, *: $P<0.05$, compared with the HFD control group).

Figure 4C:
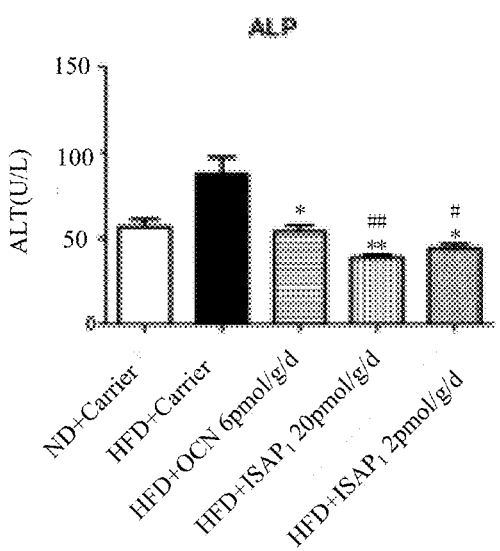

FIG. 4C shows an effect of daily intraperitoneal injection of various concentrations of SEQ ID NO.17 and OCN (mouse OCN) for 6 weeks on a level of aspartate aminotransferases (AST) in blood of the DIO-NAFLD mice fed with high-fat diet, comparing with that in the mice of the HFD control group and that in the mice of the ND control group, wherein each group includes six mice (according to statistical analysis, *: $P<0.05$, compared with the HFD control group; and #: $P<0.05$ and ##: $P<0.01$, compared with the ND control group).

Figure 4D:
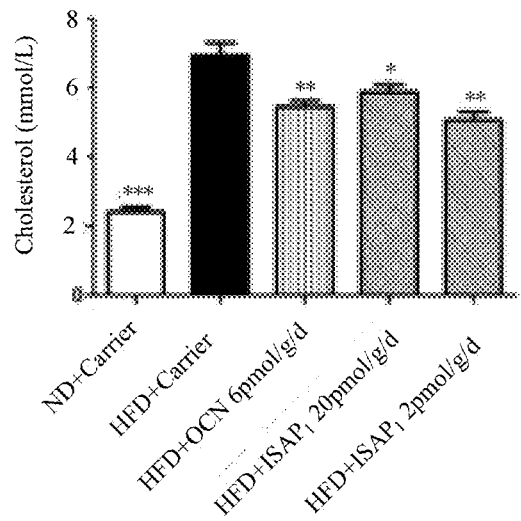

FIG. 4D shows an effect of daily i.p. injection of various concentrations of SEQ ID NO.17 and OCN (mouse OCN) for 6 weeks on a level of serum total cholesterols (TC) of the DIO-NAFLD mice fed with HFD, comparing with that in the mice of the HFD control group, wherein each group includes six mice (according to statistical analysis, *: $P<0.05$ and **: $P<0.01$, compared with the HFD control group).

Figure 4E:
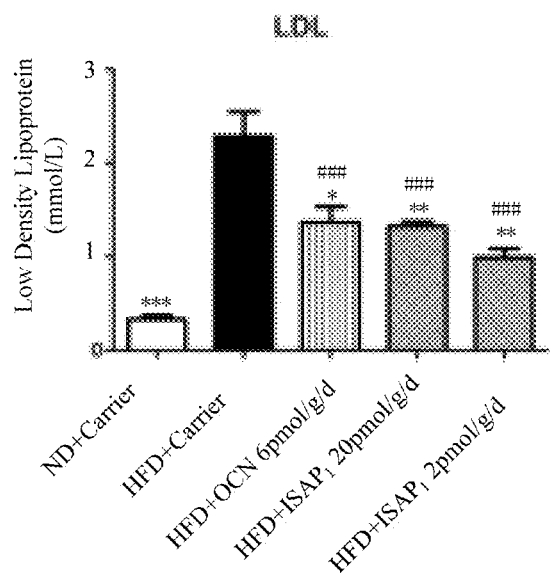

FIG. 4E shows an effect of daily i.p. injection of various concentrations of SEQ ID NO.17 and OCN (mouse OCN) for 6 weeks on a level of low density lipoprotein (LDL) of the DIO-NAFLD mice fed with HFD, comparing with that in the mice of the HFD control group and that in the mice of the ND control group, wherein each group includes six mice (according to statistical analysis, *: $P<0.05$, : $P<0.01$, and *: $P<0.001$, compared with the HFD control group; and ###: $P<0.001$, compared with the ND control group).

Figure 4F:
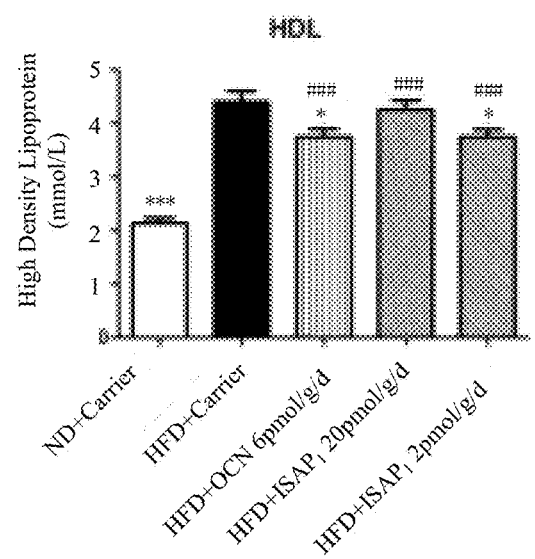

FIG. 4F shows an effect of daily i.p. injection of various concentrations of SEQ ID NO.17 and OCN (mouse OCN) for 6 weeks on a level of high density lipoprotein (HDL) of the DIO-NAFLD mice fed with HFD, comparing with that in the mice of the HFD control group and that in the mice of the ND control group, wherein each group includes six mice (according to statistical analysis, *: $P<0.05$ and ***: $P<0.001$, compared with the HFD control group; and ###: $P<0.001$, compared with the ND control group).

Figure 5A:
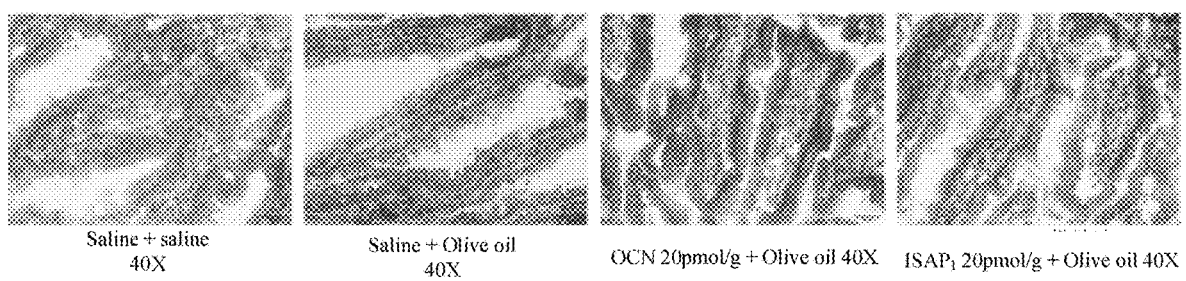

FIG. 5A shows frozen sections of jejunum segments near duodenum segments, obtained from ND-fed wild-type C57BL/6 mice gavaged with sterilized olive oil followed by i.p. injection of SEQ ID NO.17 and OCN before sacrificing and from ND-fed wild-type C57BL/6 mice in control groups, stained with oil red O and counterstained with hematoxylin.

Figure 5B:
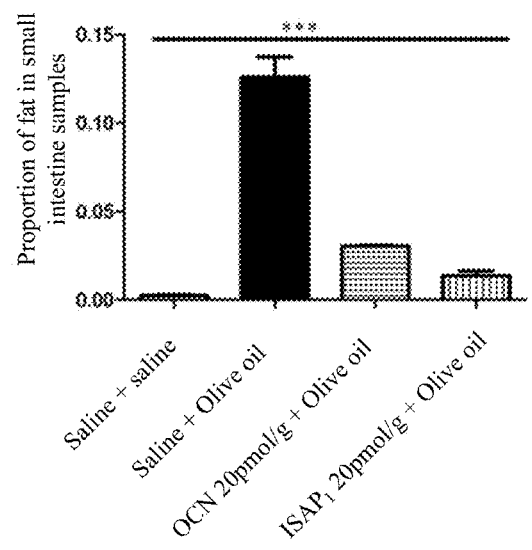

FIG. 5B shows quantification of oil red O positive areas shown in FIG. 5A by an ImageJ software under double-blind conditions, and shows a ratio of the positive areas to a total area of intestinal villi (according to statistical analysis, ***: $P<0.001$, N=3, compared with the ratio for the mice treated with normal saline and the sterile olive oil.).

Figure 6A:
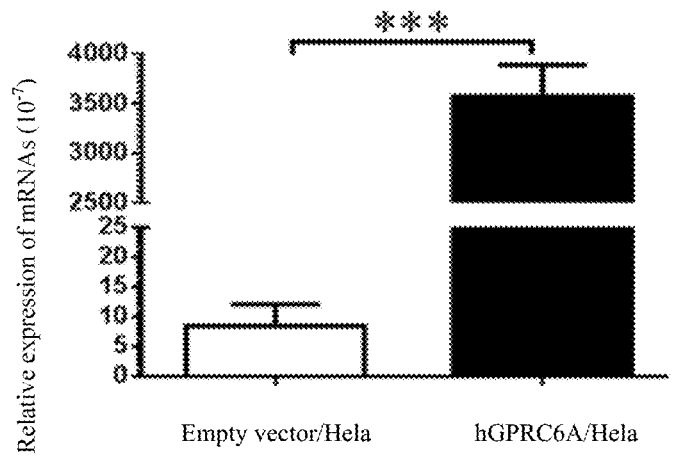

FIG. 6A shows overexpression of human GPRC6A (hPGRC6A) in Hela cells.

Figure 6B:
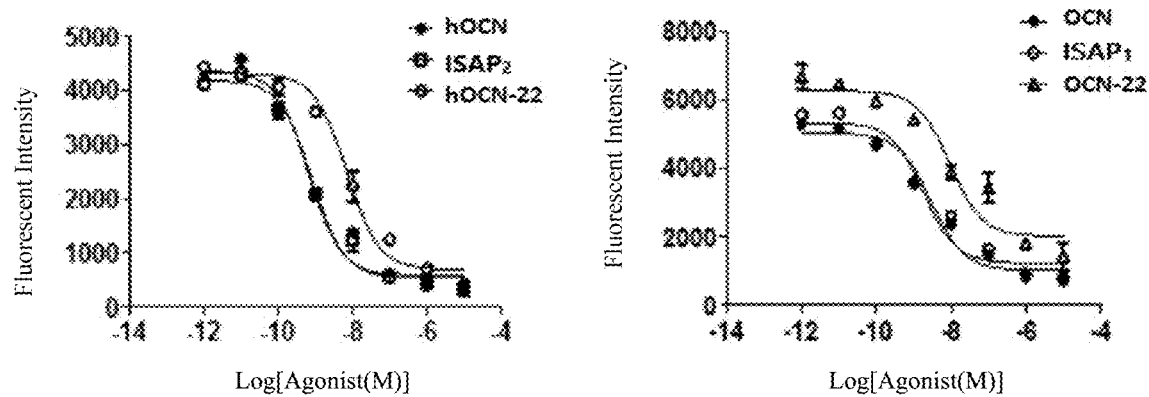

FIG. 6B shows binding of SEQ ID NO.17, OCN and OCN-22 to cell membranes of the Hela cells with hGPRC6A overexpressed and binding of SEQ ID NO.2, human OCN (hOCN) and human OCN-22 (hOCN-22) to the cell membranes of the Hela cells with hGPRC6A overexpressed.

Figure 6C:
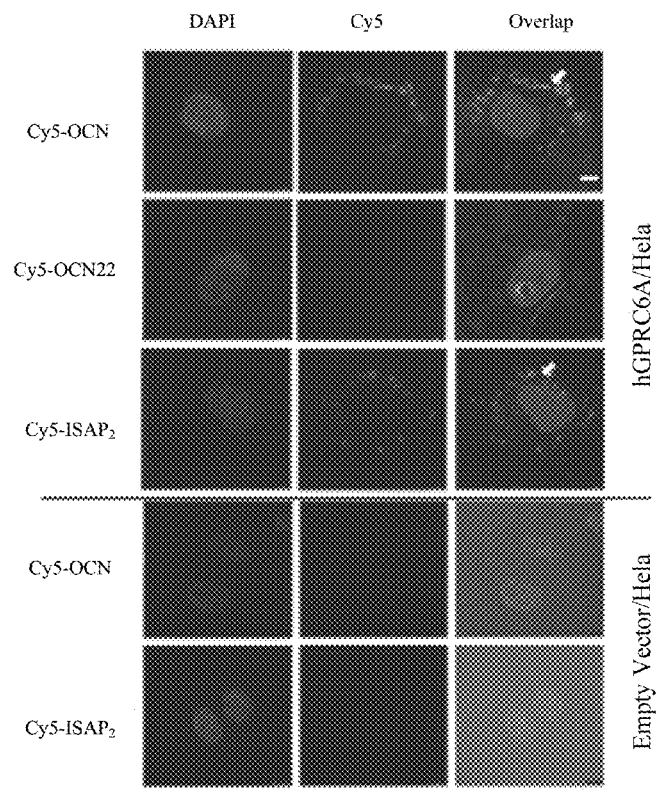

FIG. 6C shows effects of Cy-5-labeled OCN (Cy5-OCN), Cy-5-labeled OCN-22 (Cy5-OCN22), and Cy-5-labeled SEQ ID NO.2 (Cy5-SEQ ID NO.2) on GPRC6A internalization in the Hela cells with hGPRC6A overexpressed.

Figure 7A:
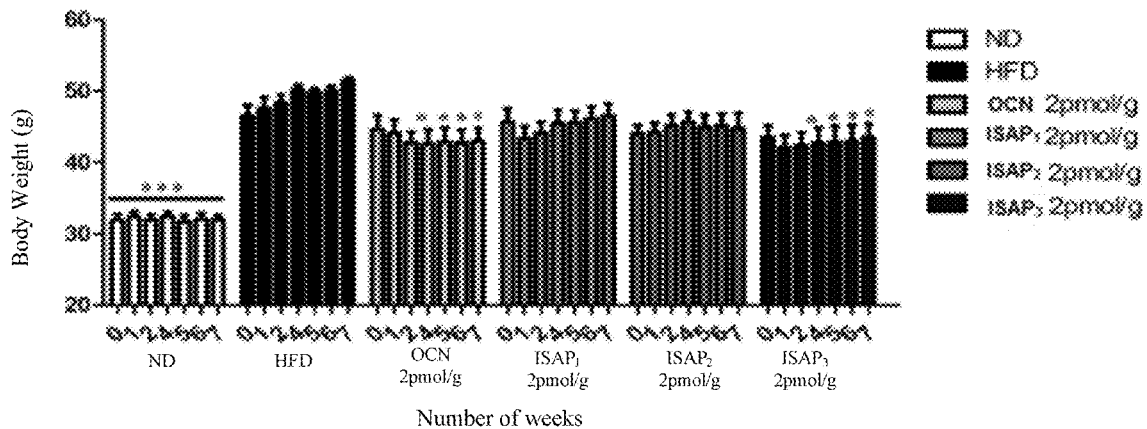

FIG. 7A shows effects of gavaged OCN, SEQ ID NO.17, SEQ ID NO.2, and SEQ ID NO.3 to mice fed with HFD and ND for 7 weeks on body weights of the mice.

Figure 7B:
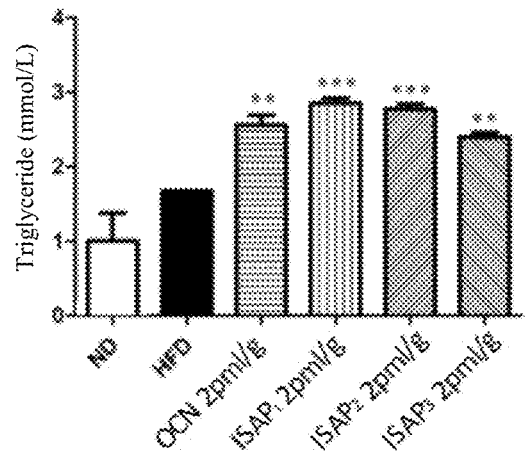

FIG. 7B shows levels of triglyceride in feces of the mice in an SEQ ID NO.17-treated HFD group, in an SEQ ID NO.2-treated HFD group, in an SEQ ID NO.3-treated HFD group, in an OCN-treated HFD group, in the HFD control group, and in the ND control group.

Figure 8:
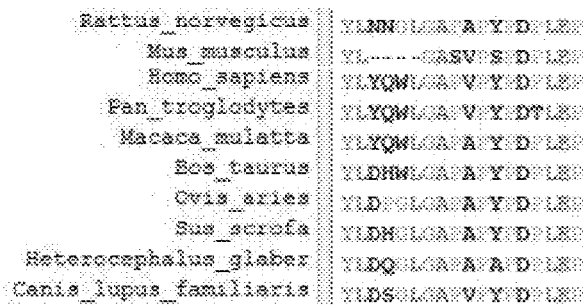

FIG. 8 shows comparison of the sequences of SEQ ID NO.4, SEQ ID NO.1, SEQ ID NO.2, SEQ ID NO.5, SEQ ID NO.7, SEQ ID NO.6, SEQ ID NO.8, SEQ ID NO.9, SEQ ID NO.10 and SEQ ID NO.11 from various species.

Figure 9:
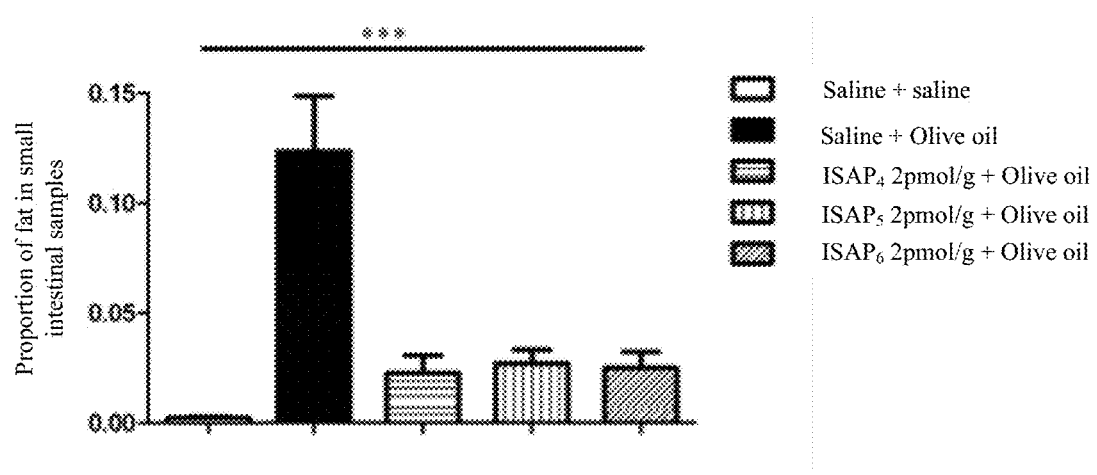

FIG. 9 shows effects of gavaged SEQ ID NO.15, SEQ ID NO.16, and SEQ ID NO.14 on a ratio of areas of the jejunum containing fat to a total area of intestinal villi of ND-fed wild-type C57BL/6 mice (according to statistical analysis, ***: $p<0.001$, and n=3, compared with the mice treated with "normal saline+the olive oil").

DETAILED DESCRIPTION

As used herein, the term "peptide that regulates fat metabolism" (also referred to as "insulin secretion association peptide (ISAP)" refers to an OCN originated or derived peptide that may regulates energy metabolism and variants of the OCN originated or derived peptide.

The term "conservative amino acid substitution" as used herein refers to the substitution of the original amino acid sequence with another amino acid residue having similar properties. For example, lysine residues, arginine residues, and histidine residues may be similar in having basic side chains. Furthermore, aspartic acid residues and glutamic acid residues may be similar in having acidic side chains. Furthermore, asparagine residues, glutamine residues, serine residues, threonine residues, tyrosine residues and cysteine residues may be similar in having uncharged polar side chains, and glycine residues, alanine residues, valine residues, leucine residues, isoleucine residues, proline residues, tryptophan residues, phenylalanine residues, and thionine residues may be similar in having non-polar side chains. Further, tyrosine residues, phenylalanine residues, tryptophan residues, and histidine residues may be similar in having aromatic side chains. Thus, it will be apparent to the skilled in the related art that amino acid substitutions made in groups of amino acids having similar properties as described above do not cause any change in properties.

Full names and abbreviations of the amino acids used in the present disclosure are listed hereafter:

| Full name | Three-letter abbreviation | One-letter abbreviation |
| --- | --- | --- |
| Serine | Ser | S |
| Threonine | Thr | T |
| Asparagine | Asn | N |
| Glutamine | Gln | Q |
| Tyrosine | Tyr | Y |
| Cysteine | Cys | C |
| Aspartic acid | Asp | D |
| Glutamate | Glu | E |
| Histidine | His | H |

| Full name | Three-letter abbreviation | One-letter abbreviation |
| --- | --- | --- |
| Lysine | Lys | K |
| Arginine | Arg | R |
| Glycine | Gly | G |
| Alanine | Ala | A |
| Valine | Val | V |
| Leucine | Leu | L |
| Isoleucine | Ile | I |
| Phenylalanine | Phe | F |
| Methionine | Met | M |
| Proline | Pro | P |
| Tryptophan | Trp | W |

The term "disease associated with abnormal fat metabolism" as used herein refers to a disease characterized by fat metabolism disorder or a complication thereof caused by genetics or environment or both, such as but not limited to obesity, Type 2 diabetes, NAFLD, insulin resistance, hypertriglyceridemia, hypercholesterolemia, atherosclerosis, and coronary heart disease.

The term "non-alcoholic fatty liver disease" as used herein refers to a clinicopathologic syndrome characterized by excessive deposition of fat in hepatocytes due to factors other than alcohols.

The term "insulin resistance" as used herein refers to a state in which cells cannot effectively "burn" glucose as insulin-mediated glucose uptaken and consumption is reduced. When insulin resistance is at a high level, the body may produce excessive insulin, leading to high blood pressure, abnormal lipidemia, heart diseases and diabetes. Especially in a case of type 2 diabetes, insulin may not function normally because muscles and adipose tissues cannot recognize an increase of the insulin.

Terms not explicitly defined herein have meanings as commonly understood by the skilled in the related art.

EMBODIMENTS

The Dulbecco's Modified Eagle Medium (DMEM) used in the present disclosure is purchased from Sigma. 10% of Fetal Bovine Serum (FBS), 1% of non-essential amino acids, 1 g of glucose, 0.75 g of sodium bicarbonate, 0.1 g of bovine serum albumin and 1.5 ml of 4-hydroxyethylpiperazineethanesulfonic acid (HEPES) may be supplemented into 500 ml of the media for cell culturing.

3T3L1 cells may be purchased from American Type Culture Collection (ATCC).

$ISAP_1$, $ISAP_2$, $ISAP_3$, $ISAP_4$, $ISAP_5$, and $ISAP_6$ may be manmade synthesized. Sequences of these peptides are listed in a following table.

TABLE I

Amino acid sequences of various ISAPs synthesized

| Peptide | SEQ ID | Amino Acid Sequence |
| --- | --- | --- |
| $ISAP_1$ | SEQ ID NO: 17 | Tyr-Leu-Gly-Ala-Ser-Val-Pro-Ser-Pro-Asp-Pro-Leu-Glu-Pro-Thr |
| $ISAP_2$ | SEQ ID NO: 2 | Tyr-Leu-Tyr-Gln-Trp-Leu-Gly-Ala-Ser-Val-Pro-Ser-Pro-Asp-Pro-Leu-Glu-Pro |
| $ISAP_3$ | SEQ ID NO: 3 | Tyr-Leu-Tyr-Gln-Trp-Leu-Gly-Ala-Ser-Val-Pro-Ser-Pro-Asp-Pro-Leu-Glu-Pro-Arg |

TABLE I-continued

Amino acid sequences of various ISAPs synthesized

| Peptide | SEQ ID | Amino Acid Sequence |
| --- | --- | --- |
| $ISAP_4$ | SEQ ID NO: 15 | Ser-Val-Pro-Ser-Pro-Asp-Pro-Leu-Glu-Pro |
| $ISAP_5$ | SEQ ID NO: 16 | Pro-Ser-Pro-Asp-Pro-Leu-Glu-Pro |
| $ISAP_6$ | SEQ ID NO: 14 | Pro-Asp-Pro-Leu-Glu-Pro |

All the animal experiments have been approved by the Animal Ethics Committee of the Shenzhen Institutes of Advanced Technology (SIAT) of the Chinese Academy of Sciences (CAS), in accordance with the requirements of the Ethics Committee.

Embodiment 1

Study of $ISAP_1$ Functions

S110: a diet-induced obesity and nonalcoholic fatty liver disease (DIO-NAFLD) mouse model by HFD feeding may be established.

Figure 1:
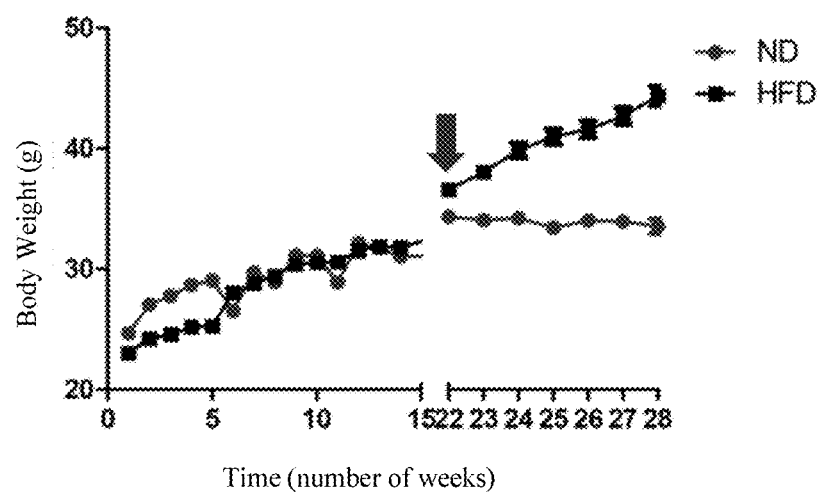
FIG. 1 shows body weight comparison of a model of C57BL/6 mice having a diet-induced-obesity and nonalcoholic fatty liver disease (DIO-NAFLD) generated by feeding with high fat diet (HFD) for 12 weeks with mice of a normal control group fed with normal diet (ND).
Figure 2A:
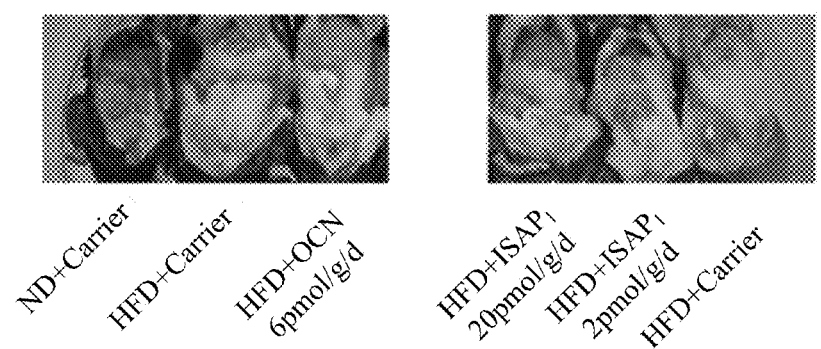
FIG. 2A shows an effect of daily intraperitoneal (i.p.) injection of various concentrations of insulin secretion association peptide 1 (SEQ ID NO.17) and OCN (mouse OCN) for 6 weeks on a size of an epididymal fat pad of a DIO-NAFLD mouse fed with high-fat diet, comparing with that of a mouse with HFD only (a HFD control group) and a mouse with ND only (a ND control group).
Figure 2B:
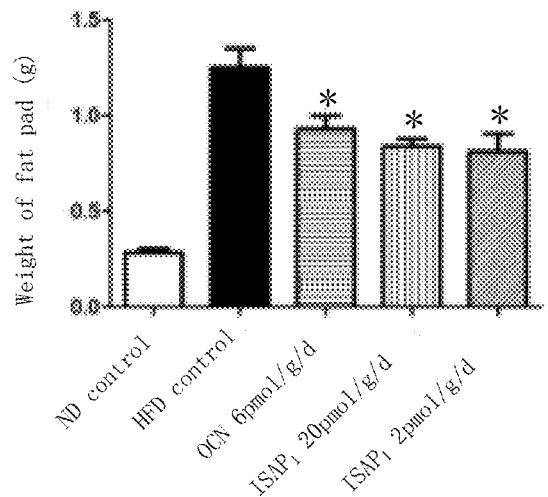
FIG. 2B shows average mass of the epididymal fat pads of the mice in SEQ ID NO.17-treated groups, in an OCN-treated group, in the HFD control group, and in the ND control group (according to statistical analysis, *: $P<0.05$, compared with the HFD control group).
Figure 2C:
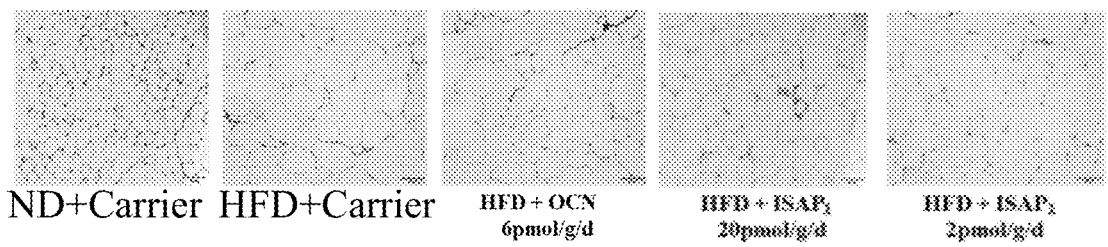
FIG. 2C shows hematoxylin and eosin (H&E) staining of an epididymal fat pad tissue slice obtained from each epididymal fat pad shown in FIG. 2A.
Figure 2D:
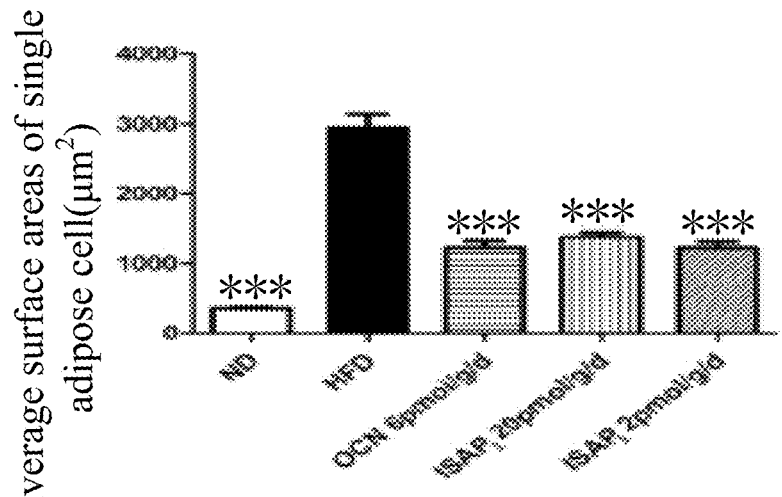
FIG. 2D shows average surface areas of each single adipocyte calculated based on the H&E staining of the epididymal fat pad tissue slice under double-blind conditions (according to statistical analysis, ***: $P<0.001$, compared with the HFD control group).

Thirty specific pathogen free (SPF) level healthy 6-week-old male C57BL/6 mice may be purchased from the Experimental Animal Center of Guangdong Province. A body mass of each mouse may be 18 g to 22 g. The mice may be divided into two groups, housed in a SPF-grade animal facility of SIAT. Six mice may be fed with ND (the ND contains 5% of fat; 53% of carbohydrate; 23% of protein, having total calories of 25 J/g) for 12 weeks to be a ND control group, and may be allowed to have food and water ad lib. The other mice may be fed with HFD (the HFD may be D12451, Research Diets, Inc.) for 12 weeks, and may be allowed to have food and water ad lib. Physiological indexes of the mice may be detected. A body weight of a mouse fed with the HFD may be 15% greater than that of a mouse fed with ND, suggesting the DIO-NAFLD mouse model may have been established successfully. In the present embodiment, an average body weight of the DIO-NAFLD mice may be more than 40 g. Comparison of average body weight of the mice of the established model with that of the mice in the ND control group is shown in FIG. 1. The arrow indicates a time point at which the HFD be started.

S120: effect of i.p. injection of $ISAP_1$ on DIO-NAFLD mice may be studied.

S121: effect of i.p. injection of $ISAP_1$ on epididymal fat pad may be studied.

When the body weight of the each mouse fed with the HFD is more than 40 g, and when the blood glucose level of the each mouse is above 10 mMol, each DIO-NAFLD mouse may be treated with i.p. injection of $ISAP_1$ for 6 consecutive weeks. The DIO-NAFLD mice may be divided into 4 groups, 6 mice in each group. $ISAP_1$ may be dissolved in normal saline solution containing 0.01% of BSA. A dosage of 20 pmol/g of $ISAP_1$ may be i.p. injected into each DIO-NAFLD mouse in group #1 once a day, and a dosage of 2 pmol/g of $ISAP_1$ may be i.p. injected into each DIO-NAFLD mouse in group #2 once a day. OCN (mouse OCN protein) may be prepared and administered similarly as the $ISAP_1$ at a dosage of 6 pmol/g to each mouse in group #3. The mice in group #4 may be treated with normal saline only as a HFD control group. After 6 weeks, the mice may be euthanized by application of 95% $CO_2$, and epididymal fat pads of 4 mice selected from each group and an epididymal fat pad of a mouse from the ND control group may collected and weighed. Paraffin slices of each epididymal fat pad may be prepared, and an area of the adipocytes may be observed by microscopy.

Experimental results are shown in FIG. 2. FIG. 2A shows overall appearances of the epididymal fat pads of the mice in the ND control group, in the HFD control group, and in the group receiving daily i.p. injection of $ISAP_1$ or OCN, wherein the administration of $ISAP_1$ may significantly reduce the size of the epididymal fat pads as compared with the HFD control group. FIG. 2B shows an average mass of the epididymal fat pads of the mice in each group, wherein the administration of ISAP1 may significantly reduce the weight of the epididymal fat pad as compared with the HFD control group. FIG. 2C shows H&E staining of the epididymal fat pads shown in FIG. 2A, revealing that the administration of $ISAP_1$ may significantly reduce sizes of adipocytes as compared with the HFD control group. FIG. 2D shows average surface areas of each single adipocytes calculated from H&E stained slices under double-blind conditions, indicating that $ISAP_1$ may significantly reduce the sizes of the adipocytes. Statistical analysis may be performed to compare with the HFD control group, wherein *: $P<0.05$, : $P<0.01$, and *: $P<0.001$.

S122: effect of i.p. injection of $ISAP_1$ on the liver may be studied.

Figure 3A:
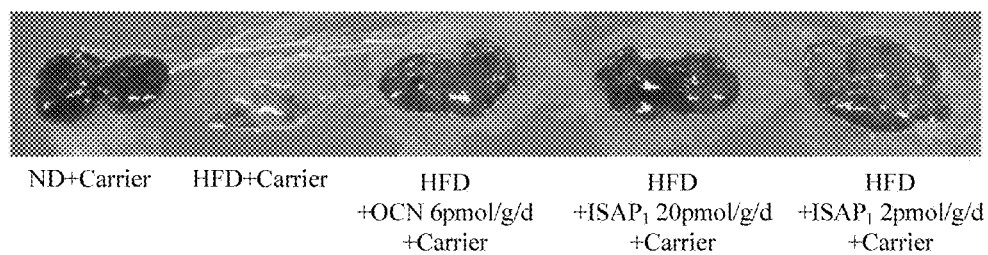
FIG. 3A shows representative images of liver appearances obtained from five mice selected from two groups with daily i.p. injection of various concentrations of SEQ ID NO.17, from a group with daily i.p. injection of OCN, from the HFD control group, and from the ND control group.
Figure 3B:
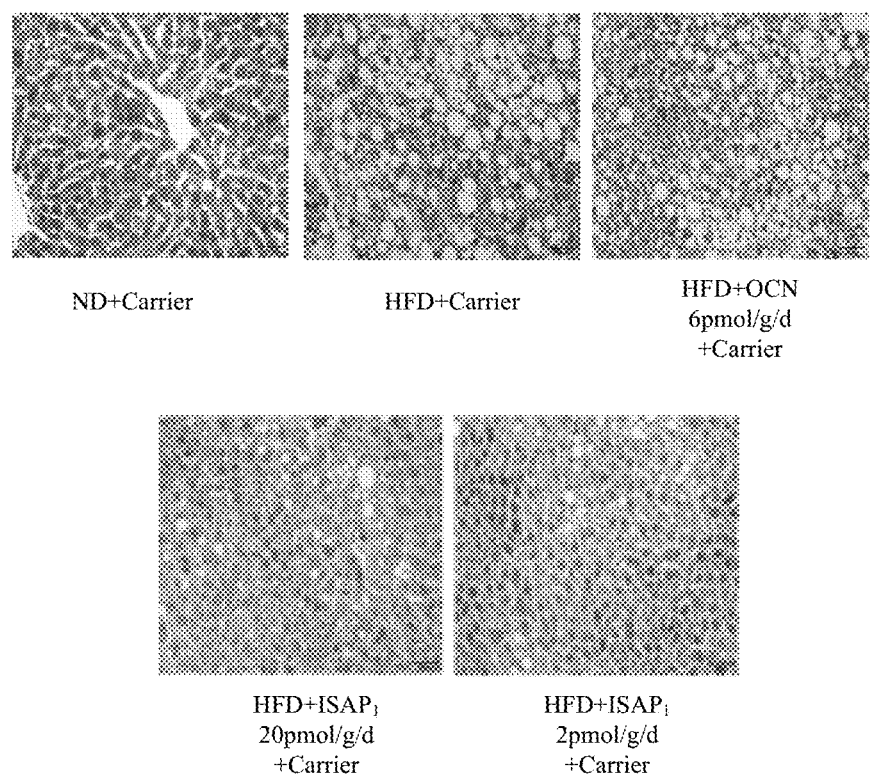
FIG. 3B shows H&E staining of liver tissue slices obtained from the livers shown in FIG. 3A.
Figure 3C:
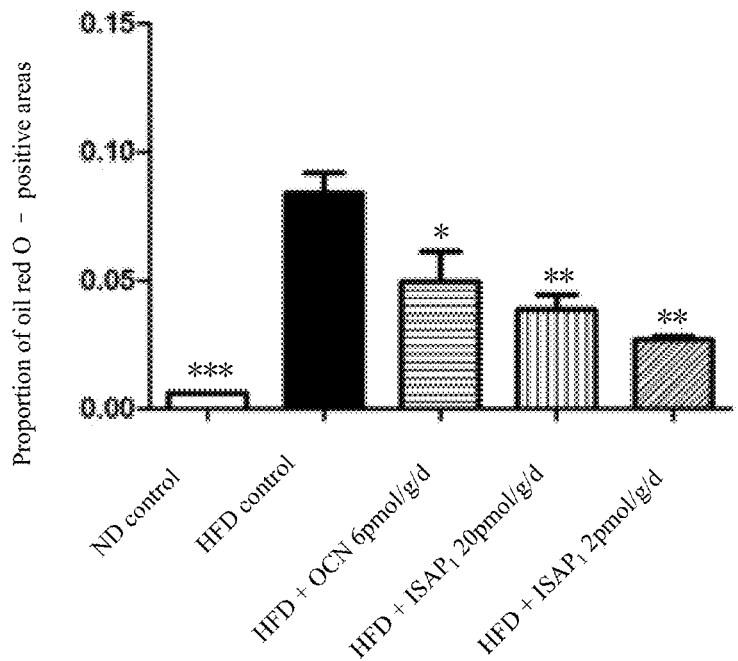
FIG. 3C shows surface areas of accumulated Oil Red 0 dye from liver cells of the mice from each group after Oil Red 0 staining under double-blind conditions, wherein each group includes six mice (according to statistical analysis, *: $P<0.05$, : $P<0.01$, and *: $P<0.001$, compared with the HFD control group).

In S121, livers may be collected while collecting the adipose tissues, and appearance of the livers may be photographed. A part of liver tissues may be taken for frozen sectioning, stained with oil red O for microscopic observation, and then a same area may be quantitatively analyzed. Results are shown in FIG. 3. FIG. 3A shows representative images of liver appearances for five mice selected from each group. The lighter the color is, the higher the fat content is contained. Treatment of HFD and a carrier (HFD+carrier) may result in significant liver fat accumulation, and i.p. injection of $ISAP_1$ may significantly reduce the liver fat accumulation. FIG. 3B shows H&E staining of a liver slice obtained from the livers shown in FIG. 3A, wherein a light color represents intracellular stained fat. FIG. 3C shows surface areas of accumulated non-alcoholic fatty liver cells obtained after liver oil red O staining under double-blind conditions from the mice in each group. It is shown that a proportion of fat in the liver of the mice in the $ISAP_1$-treated group is decreased significantly as compared with that of the mice in the HFD control group, indicating that $ISAP_1$ may reduce the fat content in hepatocytes.

S123: the effect of i.p. injection of $ISAP_1$ on liver functions and blood lipids in mice may be studied.

In S121, before sacrificing the mice, blood of each mouse may be collected from a tail vein and detected for a level of alanine aminotransferases (ALT), a level of alkaline phosphatases (ALP), a level of aspartate aminotransferases (AST), a serum level of cholesterols, a level of low-density lipoprotein (LDL), and a level of high-density lipoprotein (HDL) using a Roche blood glucose meter (model cobas8000) as per manufacturer's instructions. Experimental results are shown in FIG. 4. $ISAP_1$ may be effective in reducing the ALT, the ALP, the AST, the cholesterols, and the LDL even at the dosage of 2 pmol/g, comparing with the HFD control group.

It can be seen from the above results that i.p. injection of $ISAP_1$ can significantly affect the fat metabolism in mice, reduce fat accumulation in hepatocytes and adipocytes, improve the fat metabolism, and effectively alleviate progression of the NAFLD.

S130: binding of $ISAP_1$ to human GPRC6A (hGPRC6A) may be studied.

S131: overexpression of hGPRC6A in Hela cells may be established.

1) Cell plating: A Hela cell suspension may be plated at a density of $1.6×105$ cells/mL into a 6-well tray with 2 mL of DMEM per well, incubating at 37° C. and 5% $CO2$ for 24 hours.

2) A vector carrying hGPRC6A (pReceiver-M61) may be transfected into the Hela cells for overexpression, using Lipofectamine 2000 (Invitrogen) as per manufacturer's instructions, and media containing the vector may be replaced by normal media 4 hours later.

3) After the transfection, the cells may be cultured in the normal media for another 48 hours, and the normal media may be discarded. The cells attached on a bottom of each well may be washed twice with sterile PBS, and 300 μl of TRIzol solution may be added into each well. Cellular RNAs may be extracted as per RNAiso Plus (TaKaRa) instructions, and after a DNase treatment, may be reversely transcribed into cDNAs using DNAEngine and a SuperScript™ (Invitrogen, Canada) kit. The cDNAs may be used as a template, and real-time monitoring and analysis may be performed to fluorescent PCR products at various time points using a SYBR Green (Light Cycler Roche, Germany) method to detect expression levels of the hGPRC6A. If necessary, screening using puromycin may be performed to obtain a cell strain with stable expression of the hGPRC6A. The selected cell strain may then be detected for its gene expression by qPCR. As shown in FIG. 6A, hGPRC6A may be stably expressed in a large amount in the selected Hela cells.

S132: experiments of binding various peptides of OCN to cell membranes of Hela cells with hGPRC6A overexpressed may be performed.

To detect the binding between the peptides and the hGPRC6A, a fluorescent detection may be performed. A higher fluorescent intensity may indicate a higher level of binding of the peptides to the hGPRC6A. Further, a competitive agonist may be added into the media to competitively inhibit the peptides from binding to the hGPRC6A, and the fluorescent intensity may be reduced. Experimental results are shown in FIG. 6B. Compared with OCN, affinity of the $ISAP_1$ binding to the hGPRC6A may be consistent with that of the OCN binding to the hGPRC6A. Although hOCN-22 may bind to hGPRC6A, but affinity between hOCN-22 and hGPRC6A may be 10 times lower than that between $ISAP_1$ and hGPRC6A, suggesting that $ISAP_1$ may be a core domain of OCN to interact with the receptor hGPRC6A.

S140: effect of acute gavage of $ISAP_1$ on intestinal fat absorption in normal mice may be studied.

Six-week-old male wild-type C57BL/6 mice may be divided into four groups, three in each group, three out of the four groups of mice may be intestinally perfused with 200 μl sterilized olive oil solution (Sigma), and the other one group of mice may be intestinally perfused with normal saline solution to be a negative control group. After 30 minutes, two groups of the mice treated with sterilized olive oil solution may be i.p. injected with OCN (6 pmol/g) and $ISAP_1$ (6 pmol/g) respectively, and the other one group of the mice treated with sterilized olive oil solution may be i.p. injected with normal saline solution to be a saline control group. Further the mice of the negative control group solution may also be i.p. injected with normal saline solution to be the negative group. The mice of all four groups may be sacrificed 30 minutes later. Small intestine samples may be collected. The small intestine sample may be taken from a duodenum to a caecum, divided into 3 segments of equal length. After washing with pre-cooled normal saline solution, a segment close to the duodenum may be frozen and sliced, stained with oil red O and observed for fat absorption.

Results of the experiment are shown in FIG. 5. FIG. 5A shows jejunum samples close to the duodenum segments, collected from four mice of each group, being frozen and sliced, stained with oil red O, and counterstained with hematoxylin. FIG. 5B shows oil red O-positive areas shown in FIG. 5A being quantified by the ImageJ software under double-blind conditions, and a ratio of the oil red O-positive area to a total area of the intestinal villi in each sample may be calculated. It may be shown that, compared with the saline control group, the treatment of $ISAP_1$ may effectively reduce the mouse intestinal absorption of the olive oil, and the $ISAP_1$-induced reduction in the olive oil absorption may be even more effective than the OCN treatment.

Six-week-old male wild-type C57BL/6 mice may be divided into 6 groups, 6 mice in each group. Group #1 may be provided with ND, and groups #2 to #6 may be provided with HFD. Group #2 may be treated as a HFD control group. Groups #3 to #6 may be experimental groups, and mice in groups #3 to #6 may be gavaged with OCN, $ISAP_1$, $ISAP_2$, and $ISAP_3$ respectively at 2 pmol/g of body weight for 7 weeks. Body weight of each mouse may be monitored and measured once a week. Experimental results are shown in FIG. 7A. It may be shown from the figure that a significant weight loss occurred for the mice in the $ISAP_1$-treated group as compared with the mice in the HFD control group. *: $P<0.05$, : $P<0.01$, *: $P<0.001$.

Feces of each mouse may be collected in week 7, baked at 60° C. for 3 days to ensure complete dryness. Then, 1 mg of the feces may be collected and soaked in 1 ml of a mixed solution consisting of chloroform and methanol in a ratio of 2:1. The soaked feces may then be disrupted with a tissue homogenizer and centrifuged to obtain a supernatant. The supernatant may be detected for triglyceride by the Roche blood biochemical analyzer. Experimental results are shown in FIG. 7B. : $P<0.01$, *: $P<0.001$. Compared with the HFD control group, the content of triglyceride in the feces collected from the mice in the $ISAP_1$-treated group may be significantly increased, indicating that gavage of $ISAP_1$ may significantly reduce absorption of triglycerides through intestinal tracts.

Embodiment 2

Study of $ISAP_2$ Functions

S210: binding of $ISAP_2$ to human GPRC6A may be studied.

S211: overexpression of hGPRC6A in Hela cells may be established.

1) Cell plating: A Hela cell suspension may be plated at a density of $1.6 \times 10^5$/mL into a 6-well tray with 2 ml of DMEM media per well, incubating at 37° C. and 5% CO2 for 24 hours.

2) A vector carrying hPGRC6A (pReceiver-M61) may be transfected into the Hela cells for overexpression, using Lipofectamine 2000 (Invitrogen) as per manufacturer's instructions, and the media containing the vector may be replaced by normal media 4 hours later.

3) After the transfection, the cells may be cultured in the normal media for another 48 hours, and the media may be discarded. The Hela cells attached to a bottom of each well of the tray may be washed twice with sterile PBS, and 300 μl of TRIzol solution may be added into each well. Cellular RNAs may be extracted as per RNAiso Plus (TaKaRa) instructions. After a treatment with DNase, the extracted cellular RNAs reversely transcribed into cDNAs using DNA Engine and a SuperScript™ (Invitrogen, Canada) kit. The cDNAs may be used as a template, and real-time monitoring and analysis may be performed to fluorescent PCR products at various time points using a SYBR Green (Light Cycler Roche, Germany) method to detect expression levels of hGPRC6A. If necessary, screening using puromycin may be performed to obtain a cell strain with stable expression of hGPRC6A, and the cell strain may be detected for its gene expression by qPCR. Experimental results are shown in FIG. 6A. Human GPRC6A is stably expressed substantially in the selected Hela cells.

S220: experiments of binding of $ISAP_2$ and hOCN to cell membranes of the Hela cells with hGPRC6A overexpressed may be performed.

A method performed herein is relatively the same as the method described in the above-mentioned embodiment 1. Experimental results are shown in FIG. 6B. Compared with hOCN, the ability of $ISAP_2$ binding with cell membranes may be consistent with that of hOCN binding with the cell membranes, whereas hOCN-22 may not show such ability. Accompanying with the results of S132 in Embodiment 1, it may be suggested that IASP1 and $ISAP_2$ are the core domains of OCN and hOCN, respectively. IASP1 and $ISAP_2$ may both interact with the receptor hGPRC6A, suggesting that $ISAP_1$ and $ISAP_2$ may have a same function, leading to subsequent signaling and biological events through hGPRC6A.

S230: Cy5-labelled OCN, Cy5-labelled hOCN22, and Cy5-labelled $ISAP_2$ may promote internalization of GPRC6A in the GPRC6A-overexpressed Hela cells.

The hGPRC6A-expressed Hela cell suspension may be plated at a density of $1.6 \times 10^5$/ml into a 24-well tray, and each well of the tray may be pre-placed with a gelatin-coated coverslip. 0.5 mL of media containing the cells may be added into each well, and the cells may be incubating at 37° C. and 5% CO2 for 24 hours. The cells may be starved for 4 h in serum-free media before any treatment, and then 100 nM of Cy5-OCN, 100 nM of Cy5-hOCN22, and 100 nM of Cy5-$ISAP_2$ may be added to each well respectively to incubate with the cells at 37° C. for 30 minutes. The cells may be fixed by polyoxymethylene for 30 minutes. Afterwards, Triton X may be added to incubate with the cells for 10 minutes. The cells may be stained with 4',6-diamidino-2-phenylindole (DAPI, Sigma) for 10 seconds as per manufacturer's instructions, and observed and photographed by a fluorescence confocal microscope. Experimental results are shown in FIG. 6C. It can be shown that Cy5-OCN and Cy5-$ISAP_2$ may be distributed inside the cell, whereas Cy5-hOCN22 may be distributed extracellularly. It is again suggested that both Cy5-OCN and Cy5-$ISAP_2$ may bind to the receptor and enter the cell through internalization, thereby playing a role in regulating energy metabolism.

S240: effect of gavage of $ISAP_2$ on HFD mice may be studied.

Six-week-old male wild-type C57BL/6 mice may be divided into 6 groups, 6 in each group. Group #1 may be provided with ND to be a ND control group, and groups #2 to #6 may be provided with HFD. Group #2 may be treated as a HFD control group. Groups #3 to #6 may be treated as experimental groups and may be gavaged with OCN, $ISAP_1$, $ISAP_2$, and $ISAP_3$ respectivelyat 2 pmol/g of body weight daily for 7 weeks. Body weight may be monitored and measured once a week. Experimental results are shown in FIG. 7A. It is apparent from the figure that a significant weight loss occurred for the mice in the ISAP$_2$-treated group as compared with the HFD control group.

Feces of the mice may be collected in the 7th week of the experiment and baked at 60° C. for 3 days to ensure complete dryness. Then, 1 mg of the feces may be weighed and soaked in 1 ml of a mixed solution containing chloroform and methanol in a ratio of 2:1. The feces with the mixed solution may be disrupted by a tissue homogenizer and centrifuged to obtain a supernatant. The supernatant may be detected for triglyceride by the Roche blood biochemical analyzer. Experimental results are shown in FIG. 7B. Compared with the HFD control group, a level of triglyceride in the feces of the ISAP$_2$-treated mice may be significantly increased, indicating that gavage of ISAP$_2$ may significantly reduce the absorption of triglyceride in the intestinal tracts.

Feces of the mice may be collected in the 7th week of the experiment and baked at 60° C. for 3 days to ensure complete dryness. Then, 1 mg of the feces may be weighed and soaked in 1 ml of a mixed solution containing chloroform and methanol in a ratio of 2:1. The feces with the mixed solution may be disrupted by a tissue homogenizer and centrifuged to obtain a supernatant. The supernatant may be detected for triglyceride by the Roche blood biochemical analyzer. Experimental results are shown in FIG. 7B. Compared with the HFD control group, a level of triglyceride in the feces of the ISAP$_2$-treated mice may be significantly increased, indicating that gavage of ISAP$_2$ may significantly reduce the absorption of triglyceride in the intestinal tracts.

Embodiment 3

Study of ISAP$_3$ Functions

S310: effect of gavage of ISAP$_3$ on HFD mice may be studied.

Six-week-old male wild-type C57BL/6 mice may be divided into 6 groups, 6 in each group. Group #1 may be provided with ND to be a ND control group, groups #2 to #6 may be provided with HFD. Group #2 may be treated as a HFD control group. Groups #3 to #6 may be treated as experimental groups, and may be gavaged with OCN, ISAP$_1$, ISAP$_2$, and ISAP$_3$ respectively at 2 pmol/g of body weight daily for 7 weeks. A body weight of each mouse may be monitored and measured once a week. Experimental results are shown in FIG. 7A. It is apparent from the figure that a significant weight loss occurred for the mice in the ISAP$_3$-treated group as compared with the HFD control group.

Feces of each mouse may be collected in the 7th week of the experiment, and baked at 60° C. for 3 days to ensure complete dryness. 1 mg of the feces may be weighed and soaked in 1 ml of a mixed solution containing chloroform and methanol in a ratio of 2:1. The feces in the mixed solution may be disrupted by a tissue homogenizer and centrifuged to obtain a supernatant. The supernatant may be detected for triglyceride by the Roche blood biochemical analyzer. Experimental results are shown in FIG. 7B. Compared with the HFD control group, a level of triglyceride in the feces of the mice in the ISAP$_3$-treated group may be significantly increased, indicating that gavage of ISAP3 may significantly reduce the absorption of triglyceride in the intestinal tracts.

Amino acid sequences of ISAP$_1$, ISAP$_2$, and ISAP$_3$ may be compared. ISAP$_2$ may have 4 insertions, 2 substitutions, and 1 deletion of amino acid residues, compared with the amino acid sequence of ISAP$_1$. Amino acid sequences of ISAP$_3$ may have 4 insertions and 3 substitutions of amino acid residues, as compared with the amino acid sequence of ISAP$_1$. ISAP$_1$ may have 4 deletions, 2 substitutions, and 1 insertion of amino acid residues, as compared with ISAP$_2$. Therefore, the three peptides can be considered as variants of each other. It may be presumed that, the three sequences may be used as basis, and amino acid substitutions, insertions, and deletions known to those skilled in the art can be performed to the three sequences, with the proviso that the ability of the peptide to regulate energy metabolism is not significantly reduced, such as by no more than 40%, 30%, 20%, or 10%. Referring to FIG. 8, homologous sequences from a variety of biological sources may be compared. Minimal difference may be found among SEQ ID NO. 2: YLYQWLGAPVPYPDPLEP, SEQ ID NO. 4: YLNNGL-GAPAPYPDPLEP, SEQ ID NO. 5: YLYQWL-GAPVPYPDTLEP, SEQ ID NO. 6: YLYQWL-GAPVPYPDPLEP, SEQ ID NO. 7: YLDHWLGAPAPYPDPLEP, SEQ ID NO. 8: YLDPGL-GAPAPYPDPLEP, SEQ ID NO.9: YLDHGLGAPAPY-PDPLEP, SEQ ID NO. 10: YLDQGLGAPAPAPDPLEP, and SEQ ID NO. 11: YLDSGLGAPVPYPDPLEP. In most cases, when comparing every two sequence, the difference may be no more than four amino acid substitutions. It is therefore presumed that peptides having the above-listed sequences may have similar biological functions and should also be within the scope of the present disclosure. Preferably, the total number of deletions, substitutions and insertions may not exceed 4, such as no more than 3, 2, or 1. Further, SEQ ID NO. 1 has only one amino acid residue deleted as compared with SEQ ID NO. 17, so it may be inferred that SEQ ID NO. 1 has functions similar to SEQ ID NO 17.

Further, compared with ISAP$_2$, ISAP$_1$ can be seen as having one amino acid insertion at an end of ISAP$_2$, and ISAP$_3$ can also be seen as having one amino acid insertion at an end of ISAP$_2$. It may be indicated that several amino acid residues can be added at the end of the functional peptide, as long as the ability of modified peptides to regulate energy metabolism is not significantly reduced, for example, by no more than 40%, 30%, 20%, or 10%. Preferably no more than 5 amino acid residues, for example 4, 3, 2, 1 or 0 amino acid residues, may be added at the end of the functional peptide.

Embodiment 4

Functions of ISAP$_4$, ISAP$_5$, and ISAP$_6$

S410: effects of acute gavage of ISAP$_4$, ISAP$_5$, and ISAP$_6$ on intestinal absorption of fat in normal mice may be studied.

15 male wild-type C57BL/6 mice of 6 weeks old may be divided into 5 groups, 3 in each group. There may be 3 experimental groups, and the mice in the 3 experimental groups may be administered with ISAP$_4$, ISAP$_5$, and ISAP$_6$ at 2 pmol/g of body weight respectively. The mice in two control groups may be gavaged with an equal volume of normal saline daily for one week. On the 8th day of the experiment, 30 minutes after gavage of ISAP$_4$, ISAP$_5$, ISAP$_6$, and normal saline respectively, the mice in the three experimental groups may be gavaged with 200 µl of sterilized olive oil, the mice in one of the control groups may also be intragstrically administered with 200 µl of sterilized olive oil to be a saline control group, and the mice in the other one of the control groups may further be gavaged with 200 µl of normal saline to be a negative control group. After 50 minutes, each mouse may be euthanized using 95% CO2 and dissected to obtain small intestines. The jejunum near the duodenum may be frozen and sliced, stained with oil red O, and counterstained with hematoxylin. An oil red O-positive area may be quantified by the ImageJ software under double-blind conditions and a ratio of the oil red O-positive area to a total area of the intestinal villi may be calculated. Statistical analysis may be performed to compare with the mince in the saline+olive oil group. ***: p<0.001. N=3.

Experimental results are shown in FIG. 9. The oil red O-positive area may be quantified by the ImageJ software under double-blind conditions and the ratio of the oil red O-positive area to the total area of the intestinal villi may be calculated. It can be seen that, compared with the mice in the saline control group, $ISAP_4$, $ISAP_5$, and $ISAP_6$ may effectively reduce the absorption of olive oil in the mice, demonstrating that biological functions of $ISAP_4$, $ISAP_5$, and $ISAP_6$ may be comparable to those of $ISAP_1$, $ISAP_2$, and $ISAP_3$. Meanwhile, referring to the sequence comparison shown in FIG. 8, it can be seen that SEQ ID NO. 12: PVPYPDPLEP, SEQ ID NO. 15: SVPSPDPLEP, SEQ ID NO. 13: PYPDPLEP and SEQ ID NO. 16: PSPDPLEP are highly similar in sequence, and these sequences may be very conservative in various species. Therefore, they should have similar biological activities, such that these peptides and variants thereof may be considered to have an effect on the absorption and metabolism of fat by oral administration. That is to say, amino acid substitutions, insertions and deletions well known to those skilled in the related art can be performed to the sequences, with the proviso that the ability of modified peptides to regulate energy metabolism is not significantly reduced, for example, by no more than 40%, 30%, 20%, or 10%. Moreover, $ISAP_4$, $ISAP_5$, and $ISAP_6$ have shorter sequences, so costs of production may be reduced, and $ISAP_4$, $ISAP_5$, and $ISAP_6$ may exhibit better stability, and have great potential for the preparation of drugs for treating diseases associated with abnormal fat metabolism.

All publications and patents mentioned herein are hereby incorporated by reference in their entirety, as if each individual publication or patent is specifically and individually incorporated by reference. In case of conflict, the present application, including any definitions herein, shall prevail.

Although some specific embodiments of the present disclosure have been clearly disclosed herein, the above specification is illustrative rather than restrictive. For those skilled in the art, many variations of the present disclosure will be apparent by reading the description and appended claims. The full scope of the present disclosure should be determined by referring to the claims, the full scope of their equivalents, and the description and such variations.

What is claimed is:

1. A peptide for regulating fat metabolism, wherein the peptide consists of the sequence selected from the group consisting of:

(SEQ ID NO: 1)
YLGASVPSPDPLEP;

(SEQ ID NO: 4)
YLNNGLGAPAPYPDPLEP;

(SEQ ID NO: 14)
PDPLEP;
and (SEQ ID NO: 16)
PSPDPLEP.

\* \* \* \* \*

SEQUENCE LISTING

<160> NUMBER OF SEQ ID NOS: 17

<210> SEQ ID NO 1
<211> LENGTH: 14
<212> TYPE: PRT
<213> ORGANISM: Mus musculus

<400> SEQUENCE: 1

Tyr Leu Gly Ala Ser Val Pro Ser Pro Asp Pro Leu Glu Pro
1               5                   10

<210> SEQ ID NO 2
<211> LENGTH: 18
<212> TYPE: PRT
<213> ORGANISM: Homo sapiens

<400> SEQUENCE: 2

Tyr Leu Tyr Gln Trp Leu Gly Ala Pro Val Pro Tyr Pro Asp Pro Leu
1               5                   10                  15

Glu Pro

<210> SEQ ID NO 3
<211> LENGTH: 19
<212> TYPE: PRT
<213> ORGANISM: Artificial sequence
<220> FEATURE:
<223> OTHER INFORMATION: ISAP3

<400> SEQUENCE: 3

Tyr Leu Tyr Gln Trp Leu Gly Ala Pro Val Pro Tyr Pro Asp Pro Leu
1               5                   10                  15

Glu Pro Arg

<210> SEQ ID NO 4
<211> LENGTH: 18
<212> TYPE: PRT
<213> ORGANISM: Rattus norvegicus

```
<400> SEQUENCE: 4

Tyr Leu Asn Asn Gly Leu Gly Ala Pro Ala Pro Tyr Pro Asp Pro Leu
1               5                   10                  15

Glu Pro

<210> SEQ ID NO 5
<211> LENGTH: 18
<212> TYPE: PRT
<213> ORGANISM: Pan troglodytes

<400> SEQUENCE: 5

Tyr Leu Tyr Gln Trp Leu Gly Ala Pro Val Pro Tyr Pro Asp Thr Leu
1               5                   10                  15

Glu Pro

<210> SEQ ID NO 6
<211> LENGTH: 18
<212> TYPE: PRT
<213> ORGANISM: Macaca mulatta

<400> SEQUENCE: 6

Tyr Leu Tyr Gln Trp Leu Gly Ala Pro Val Pro Tyr Pro Asp Pro Leu
1               5                   10                  15

Glu Pro

<210> SEQ ID NO 7
<211> LENGTH: 18
<212> TYPE: PRT
<213> ORGANISM: Bos taurus

<400> SEQUENCE: 7

Tyr Leu Asp His Trp Leu Gly Ala Pro Ala Pro Tyr Pro Asp Pro Leu
1               5                   10                  15

Glu Pro

<210> SEQ ID NO 8
<211> LENGTH: 18
<212> TYPE: PRT
<213> ORGANISM: Ovis aries

<400> SEQUENCE: 8

Tyr Leu Asp Pro Gly Leu Gly Ala Pro Ala Pro Tyr Pro Asp Pro Leu
1               5                   10                  15

Glu Pro

<210> SEQ ID NO 9
<211> LENGTH: 18
<212> TYPE: PRT
<213> ORGANISM: Sus scrofa

<400> SEQUENCE: 9

Tyr Leu Asp His Gly Leu Gly Ala Pro Ala Pro Tyr Pro Asp Pro Leu
1               5                   10                  15

Glu Pro

<210> SEQ ID NO 10
<211> LENGTH: 18
<212> TYPE: PRT
<213> ORGANISM: Heterocephalus glaber

<400> SEQUENCE: 10
```

Tyr Leu Asp Gln Gly Leu Gly Ala Pro Ala Pro Ala Pro Asp Pro Leu
1               5                   10                  15

Glu Pro

<210> SEQ ID NO 11
<211> LENGTH: 18
<212> TYPE: PRT
<213> ORGANISM: Canis lupus

<400> SEQUENCE: 11

Tyr Leu Asp Ser Gly Leu Gly Ala Pro Val Pro Tyr Pro Asp Pro Leu
1               5                   10                  15

Glu Pro

<210> SEQ ID NO 12
<211> LENGTH: 10
<212> TYPE: PRT
<213> ORGANISM: Homo sapiens

<400> SEQUENCE: 12

Pro Val Pro Tyr Pro Asp Pro Leu Glu Pro
1               5                   10

<210> SEQ ID NO 13
<211> LENGTH: 8
<212> TYPE: PRT
<213> ORGANISM: Homo sapiens

<400> SEQUENCE: 13

Pro Tyr Pro Asp Pro Leu Glu Pro
1               5

<210> SEQ ID NO 14
<211> LENGTH: 6
<212> TYPE: PRT
<213> ORGANISM: Artificial sequence
<220> FEATURE:
<223> OTHER INFORMATION: IASP6

<400> SEQUENCE: 14

Pro Asp Pro Leu Glu Pro
1               5

<210> SEQ ID NO 15
<211> LENGTH: 10
<212> TYPE: PRT
<213> ORGANISM: Mus musculus

<400> SEQUENCE: 15

Ser Val Pro Ser Pro Asp Pro Leu Glu Pro
1               5                   10

<210> SEQ ID NO 16
<211> LENGTH: 8
<212> TYPE: PRT
<213> ORGANISM: Mus musculus

<400> SEQUENCE: 16

Pro Ser Pro Asp Pro Leu Glu Pro
1               5

<210> SEQ ID NO 17
<211> LENGTH: 15

```
<212> TYPE: PRT
<213> ORGANISM: Mus musculus

<400> SEQUENCE: 17

Tyr Leu Gly Ala Ser Val Pro Ser Pro Asp Pro Leu Glu Pro Thr
1               5                   10                  15
```